US008974801B2

(12) United States Patent
Zhang et al.

(10) Patent No.: US 8,974,801 B2
(45) Date of Patent: Mar. 10, 2015

(54) LONG TERM SUSTAINED RELEASE PHARMACEUTICAL COMPOSITION CONTAINING AQUEOUS SUSPENSION OF BISPHOSPHONATE (75) Inventors: Jack Yongfeng Zhang, Diamond Bar, CA (US); Mary Ziping Luo, Diamond Bar, CA (US); Dingyuan Fei, Montclair, CA (US); Kevin Xie, Anaheim, CA (US); Jie Fei Ding, Riverside, CA (US)

(73) Assignee: Amphastar Pharmaceuticals Inc., Rancho Cucamonga, CA (US)

( * ) Notice: Subject to any disclaimer, the term of this patent is extended or adjusted under 35 U.S.C. 154(b) by 316 days.

(21) Appl. No.: 11/768,181

(22) Filed: Jun. 25, 2007

(65) Prior Publication Data
US 2008/0153784 A1 Jun. 26, 2008

Related U.S. Application Data (60) Provisional application No. 60/876,800, filed on Dec. 21, 2006.

(51) Int. Cl.
*A61K 31/663* (2006.01)
*A61K 33/42* (2006.01)
*A61K 9/00* (2006.01)
*A61K 9/10* (2006.01)

(52) U.S. Cl.
CPC ............ *A61K 31/663* (2013.01); *A61K 9/0019* (2013.01); *A61K 33/42* (2013.01); *A61K 9/10* (2013.01)
USPC ............................ 424/400; 514/108; 423/299

(58) Field of Classification Search
CPC .... A61K 31/663; A61K 9/0019; A61K 33/42
See application file for complete search history.

(56) References Cited

U.S. PATENT DOCUMENTS

| | | | |
|---|---|---|---|
| 5,356,887 A | 10/1994 | Brenner et al. | |
| 5,462,932 A | 10/1995 | Brenner et al. | |
| 6,194,004 B1 | 2/2001 | Bechard et al. | |
| 6,201,039 B1 * | 3/2001 | Brown et al. | 523/115 |
| 6,350,471 B1 | 2/2002 | Seth | |
| 6,372,728 B1 | 4/2002 | Ungell | |
| 6,476,006 B2 | 11/2002 | Flashner-Barak et al. | |
| 6,558,702 B2 | 5/2003 | Dasch et al. | |
| 6,596,314 B2 | 7/2003 | Wong et al. | |
| 6,676,970 B2 * | 1/2004 | Bader et al. | 424/488 |
| 6,677,320 B2 | 1/2004 | Diederich et al. | |
| 6,692,767 B2 | 2/2004 | Burnside et al. | |
| 6,699,500 B2 | 3/2004 | Okada et al. | |
| 6,699,850 B2 | 3/2004 | Reszka et al. | |
| 6,706,283 B1 | 3/2004 | Appel et al. | |
| 2003/0175340 A1 * | 9/2003 | McCallister et al. | 424/466 |
| 2005/0037089 A1 | 2/2005 | Jobbins | |
| 2005/0234021 A1 | 10/2005 | Petasis | |
| 2005/0261250 A1 | 11/2005 | Daifotis et al. | |
| 2005/0282783 A1 | 12/2005 | Bujoli et al. | |
| 2006/0188542 A1 * | 8/2006 | Bobyn et al. | 424/423 |

FOREIGN PATENT DOCUMENTS

| | | |
|---|---|---|
| CA | 2427161 | 6/2002 |
| EP | 1201231 A2 | 5/2002 |
| JP | 2002-138042 | 5/2002 |
| JP | 2005-531510 | 10/2005 |

OTHER PUBLICATIONS

International Search Report dated Apr. 10, 2008 for PCT Application No. PCT/US07/25569.
Japanese Office Action dated Dec. 11, 2012 of the corresponding Japanese Patent Application No. 2009-542815, noting listed references in this IDS, with English translation (7 pages).
Josse, Solen et al., "Novel biomaterials for bisphosphonate delivery," Biomaterials, May 2005, vol. 26, Issue 14, p. 2073-2080.
Seshima, H. et al., "Adsorption and Release Properties on the Bisphosphonate-Hydroxyapatite Comprex.," Mar. 2003, $41^{st}$, vol. 22, No. 2, p. 52 (Partial Translation).
Seshima, Hisashi et al., "Control of Bisphosphonate Release Using Hydroxyapatite Granules," Journal of Biomedical Materials Research Part B: Applied Biomaterials, Mar. 2006, 78(B), p. 215-221.
Canadian Office Action dated Oct. 4, 2013 of the corresponding Canadian Patent Application No. 2673058, noting listed reference in this IDS (3 pages).
Chapurlat, R.D., Clinical Pharmacology of Potent New Bisphosphonates for Postmenopausal Osteoporosis, *Treat Endocrinol 2005*. pp. 115-125.
Merck & Co., Inc., Fosomax® (Alendronate Sodium) Tablets and Oral Solution (1995, 1997, 2000). pp. 1-22.
Blank, M.A. Ph.D., Ems B.L., et al. Nonclinical Model for Assessing Gastric Effects of Bisphosphonates, Digestive Diseases and Sciences, Feb. 1997; vol. 42 No. 2. pp. 281-288.
Devogelaer, Jean-Pierre, Modem Therapy for Paget's Disease of Bone, Focus on Bisphosphonates., *Treat Endocrino 20021*. pp. 241-257.
Rosen C.J. and Kessenich C.R., Comparative Clinical Pharmacology and Therapeutic Use of Bisphosphonates in Metabolic Bone Diseases. *Drugs* Apr. 1996, vol. 51, No. 4. pp. 537-551.
Singer, Fredrick R., M.D. and Minoofar, Payam N., Bisphosphonates in the Treatment of Disorders of Mineral Metabolism, *Advances in Endocrinology and Metabolism 1995*; vol. 6. pp. 259-288.
Thiebaud, D., et al. Three Monthly Intravenous Injections of Ibandronate in the Treatment of Postmenopausal Osteoporosis. *The American Journal of Medicine*. Oct. 1997, vol. 103. pp. 298-307.
Pecherstorfer, Martin. et al. Administration of the Bishosphonate Ibandronate (BM 21.0955) by Intravenous Bolus Injection, *Journal of Bone and Mineral Research*, vol. 11. No. 5, 1996. pp. 587-593.

(Continued)

*Primary Examiner* — David J Blanchard
*Assistant Examiner* — Barbara Frazier
(74) *Attorney, Agent, or Firm* — Christie, Parker & Hale, LLP (57) ABSTRACT

Pharmaceutical compositions for long-term sustained release of bisphosphonate drugs are provided. In one embodiment, the composition includes an aqueous suspension of a solid which includes a salt of a bisphosphonate drug and a salt of pentavalent phosphorus oxoacid. The compositions can be used to treat a variety of bone diseases, including osteoporosis.

9 Claims, 3 Drawing Sheets

(56) References Cited

OTHER PUBLICATIONS

Adami, S., et al. Efficacy and safety of ibandronate given by intravenous injection once every 3 months, *Bone* 34, 2004. pp. 881-889.

US Pharmacopoeia, <88> Biologocial Reactivity Tests, In Vivo. pp. 1-7 (accessed Mar. 25, 2008).

Ruggiero, Salvatore L. et al., Osteonecrosis of the Jaws Associated with the Use of Bisphosphonates: A Review of 63 Cases, Journal of Oral and Maxillofacial Surgeons 2004. pp. 527-534.

Bamias, Aristotle, et al., Osteonecrosis of the Jaw in Cancer After Treatment With Bisphosphonates: Incidence and Risk Factors, Journal of Clinical Oncology, vol. 3 No. 34. pp. 8580-8587 (2005).

* cited by examiner

Figure 1. X-ray Powder Diffraction Spectra of an Embodiment of Claimed Sosoloid

Figure 2 X-ray diffraction patterns for the HAp granules.

Fig. 3 Efficacy of AC-PC Complex: BMD Change, Femur of OVX Rats

LONG TERM SUSTAINED RELEASE PHARMACEUTICAL COMPOSITION CONTAINING AQUEOUS SUSPENSION OF BISPHOSPHONATE

CROSS-REFERENCE TO RELATED APPLICATION

This application claims priority to and the benefit of U.S. Provisional Application Ser. No. 60/876,800, filed on Dec. 21, 2006 in the U.S. Patent and Trademark Office, and titled "LONG TERM SUSTAINED RELEASE PHARMACEUTICAL COMPOSITION CONTAINING AQUEOUS SUSPENSION OF BISPHOSPHONATE," the entire content of which is incorporated herein by reference.

TECHNICAL FIELD

The present invention relates to sterile pharmaceutical compositions for the long term sustained release of bisphosphonate drugs. More particularly, the present invention relates to long term sustained release formulations of bisphosphonate drugs for the treatment and prevention of osteoporosis and other related bone diseases.

BACKGROUND

Osteoporosis is a bone disease characterized by low bone mass and structural deterioration of bone tissue, leading to increased bone fragility and susceptibility to fracture, especially in the spine, hip and wrist areas. Osteoporosis is a major public health and economic problem. According to the US National Osteoporosis Foundation, osteoporosis affects about 44million Americans. It is estimated that 10 million individuals in the U.S. already have the disease and almost 34 million more are estimated to have low bone mass, placing them at increased risk for osteoporosis. Approximately 80% of those affected by osteoporosis are women. Data indicates that one out of every two women and one in four men over 50 will have an osteoporosis related fracture in their lifetime. However, osteoporosis can strike at any age. Osteoporosis is responsible for more than 1.5 million fractures annually. The estimated national direct expenditures (hospitals and nursing homes) for osteoporosis and related fractures total about $14 billion each year.

Osteoporosis and/or other related bone diseases lower a patient's quality of life, making the prevention and/or treatment of the diseases an important subject matter. Many alternatives are available to prevent and/or treat osteoporosis such as: Estrogen/Hormone Replacement Therapy (ERT/HRT) commercially available under the name Estrace®, Estraderm®, Premarin® etc.; Selective Estrogen Receptor Modulators (SERMs) commercially available under the name Evista®; bisphosphonates commercially available under the name Fosamax®, Boniva®, Actonel® etc. Other medications are also available such as calcitonin commercially available under the name Miacalcin®; calcium supplements; vitamin D; and sodium fluoride.

Bisphosphonates appear to be one of the most effective and popular options for the prevention and/or treatment of osteoporosis and other related diseases such as Paget's disease, malignant hypercalcemia and metastatic bone disease, etc. Currently marketed bisphosphonates are available for oral or intravenous administration. Oral administration is generally favorable due to its ease of administration. However, oral administration of bisphosphonates is associated with low bioavailability and is also known to cause gastrointestinal related side effects including: esophagitis, esophageal ulceration, retrosternal pain, and local irritation of the upper gastrointestinal mucosa. In addition, administration of bisphosphonates involves complicated and inconvenient procedures. Under the best conditions, oral bioavailability of bisphosphonates like Fosamax®, Boniva® and Actonel® is less than 1%, and bioavailability is even less if the recommendations for administration are not followed. It is estimated that only about 50% of orally absorbed bisphosphonates reach the therapeutic sites, while the rest is excreted in the urine.

Intravenous ("IV") administration of bisphosphonates is common for the treatment of hypercalcemia but is not the normal method of administration for the treatment of osteoporosis. Furthermore, IV administration of bisphosphonates involves complicated and inconvenient administration procedures and is associated with more adverse effects, such as osteonecrosis of the Jaw ("ONJ"). It has been reported that 97% of ONJ related to bisphosphonate drugs were affiliated with IV administration. In either administration, the drug reaches its peak in a short period of time and is cleared out of the system within a couple of hours.

Due to their poor bioavailability, bisphosphonate drugs need to be continuously administered for years to be effective in the prevention/treatment of osteoporosis. However, due to their inconvenient administration requirements and associated side effects, their application for long term prevention and treatment in patients with osteoporosis is challenging and limited.

SUMMARY OF THE INVENTION

According to certain embodiments of the present invention, administration of the bisphosphonate drugs is needed only once every several months, and the side effects of the bisphosphonates are substantially reduced or eliminated. As such, some embodiments of the present invention provide invaluable long term benefits including increased bone mineral density and reduced fractures.

Certain embodiments of the present invention relate to sterile pharmaceutical compositions for the long term sustained release of bisphosphonate drugs through intramuscular administration. In one embodiment, the pharmaceutical composition comprises an aqueous suspension of a bisphosphonate drug. In another embodiment, the present invention is directed to a long term sustained release pharmaceutical composition comprising an aqueous suspension of a solid consisting of a salt of a bisphosphonate drug and a salt of pentavalent phosphorus oxoacid. The aqueous suspension of the solid is adapted to release the bisphosphonate drug into the patient over an extended period of time, for example over about two months or longer. The composition is suitable for intramuscular administration and is useful for the treatment and prevention of osteoporosis and other bone related diseases.

According to one embodiment, the bisphosphonate drug has a general structure, in its acid form (bisphosphonic acid) of $(HO)_2PO-R-OP(OH)_2$, where R can include various groups such that the bisphosphonate includes but is not limited to, pamidronic acid, alendronic acid, ibandronic acid, risedronic acid, zoledronic acid, and tiludronic acid.

One embodiment of the present invention is directed to a long term sustained release pharmaceutical composition comprising an aqueous suspension of a salt of a bisphosphonate drug and a salt of pentavalent phosphorus oxoacid, wherein the salts are salts of calcium, zinc, magnesium and combinations thereof. The salts of the bisphosphonate drugs include, but are not limited to, normal salts, acidic salts, basic salts and combinations thereof. The salts of the bisphosphonate drugs may also include anhydrous salts, hydrates and combinations of hydrates. The salts of pentavalent phosphorus oxoacid include, but are not limited to, normal salts, acidic salts, basic salts and combinations thereof. The salts of pentavalent phosphorus oxoacid may also include phosphates, pyrophosphates, metaphosphates, polyphosphates and combinations thereof. Additionally, the salts of pentavalent phosphorus oxoacid may include anhydrous salts, hydrates and combinations of hydrates.

Nonlimiting examples of suitable salts of pentavalent phosphorus oxoacid include dicalcium phosphate dihydrate, dicalcium phosphate anhydrate, octacalcium phosphate, α-tricalcium phosphate, β-tricalcium phosphate, amorphous calcium phosphate, calcium-deficient hydroxyapatite, hydroxyapatite, and tetracalcium phosphate.

Another embodiment of the present invention is directed to a long term sustained release pharmaceutical composition comprising a solid including a salt of a bisphosphonate drug and a salt of pentavalent phosphorus oxoacid, wherein the solid has a solubility in saline of less than about 0.05% by weight as bisphosphonic acid. The solid can be amorphous, crystalline (in which it may have a variety of crystal structures), or a mixture thereof. In one embodiment, the solid has a particle size of less than about 100 micrometers.

Still another embodiment of the present invention is directed to a long term sustained release composition in which the solid is suspended in an aqueous medium and has a pH ranging from about 6.0 to about 9.5. One aqueous medium for the composition of the present invention is water for injection, U.S.P.

The sustained release pharmaceutical composition according to one embodiment may further have a weight ratio of calcium to phosphorus ranging from about 0.5 to about 3.0.

The composition according to one embodiment may also include one or more inactive pharmaceutical excipients. Nonlimiting examples of suitable excipients include surfactants, suspending agents, dispersing agents, tonicity agents, preservatives, pH buffers, agents for adjusting osmotic pressure, agents for adjusting viscosity, agents for adjusting density, and the like.

Another embodiment of the present invention is directed to a method of preparing the composition. Nonlimiting examples of suitable methods include co-precipitation, co-crystallization, diffusion, infiltration, adsorption and the like.

In sum, in one embodiment of the present invention, a sterile pharmaceutical composition comprises an aqueous suspension of a bisphosphonate drug for injectable administration. The composition is a solid that includes a bisphosphonate salt and a salt of pentavalent phosphorus oxoacid. The composition is for the sustained release of the bisphosphonate salt. The solid has low solubility, i.e. less than about 0.05% in saline by weight and as the bisphosphonic acid.

According to one embodiment, the bisphosphonate drug has a general structure, in its acid form (bisphosphonic acid), of In the Formula, R can have various structures, including any bisphosphonate, including, but not limited to:

1-hydroxy-4-amino-butylidene (Alendronic acid),
1-hydroxy-3-(methylpentylamino)propylidene (Ibandronic acid),
1-hydroxy-3-amino-1-propylidene (Pamidronic acid),
1-hydroxy-2-(3-pyridinyl)-ethylene (Risedronic acid),
4-chloro-phenyl)-thio-methylene (Tiludronic acid)
1-hydroxy-2-imidazol-1-yl-ethylene (Zoledronic acid).

In another embodiment, the salts can be salts of calcium, zinc, magnesium and combinations thereof. The salt of the bisphosphonate drug may be a normal salt, an acidic salt, a basic salt or a combination thereof. The salt of the bisphosphonate drug may be an anhydrous salt, a hydrate, or a combination of various hydrates of bisphosphonic drugs. The salt of pentavalent phosphorus oxoacid may be a phosphate, a pyrophosphate, a metaphosphate, a polyphosphate or a combination thereof. The salt of pentavalent phosphorus oxoacid can be a normal salt, an acidic salt, a basic salt or a combination thereof. The salt of pentavalent phosphorus oxoacid may be an anhydrous salt, a hydrate, or a combination of various hydrates. Nonlimiting examples of suitable salts of pentavalent phosphorus oxoacid include:

dicalcium phosphate dihydrate (DCPD), $CaHPO_4 \cdot 2H_2O$
dicalcium phosphate anhydrate (DCPA), $CaHPO_4$
octacalcium phosphate (OCP), $Ca_8(HPO_4)_2(PO_4)_4 \cdot 5H_2O$
α-Tricalcium phosphate (α-TCP), $\alpha\text{-}Ca_3(PO_4)_2$
β-Tricalcium phosphate (β-TCP), $\beta\text{-}Ca_3(PO_4)_2$
amorphous calcium phosphate (ACP), $Ca_x(PO_4)_y \cdot nH_2O$
calcium-deficient hydroxyapatite (CDHA), $Ca_{10-x}(HPO_4)(PO_4)_{6-x}(OH)_{2-x} (x=0\sim1)$
hydroxyapatite (HA), $Ca_{10}(PO_4)_6(OH)_2$
tetracalcium phosphate (JTCP), $Ca_4(PO_4)_2O$ In one embodiment, the solid can be amorphous or crystalline having various crystal structures, or a mixture thereof.

According to one embodiment, the weight percentage of the salt of the bisphosphonate drug in the composition is less than about 50%. The weight ratio of calcium to phosphorus in the composition ranges from about 0.5 to about 3.0. The average particle size of the composition ranges from about 1 to about 100 micrometers.

In one embodiment, the pharmaceutical aqueous vehicle in the sterile pharmaceutical aqueous suspension of the composition is water for Injection, U.S.P. The pH of the sterile pharmaceutical aqueous suspension composition for injectable administration ranges from about 6.0 to about 9.5.

In another embodiment, the sterile pharmaceutical aqueous suspension of the composition may contain various inactive pharmaceutical excipients, such as surfactants, suspending agents, dispersing agents, tonicity agents, preservatives, pH buffers, agents for adjusting osmotic pressure, agents for adjusting viscosity, agents for adjusting density, etc.

The composition can be prepared by any suitable means, including but not limited to co-precipitation, co-crystallization, diffusion, infiltration, etc.

According to one embodiment, a sterile pharmaceutical aqueous suspension composition for injectable administration of bisphosphonate drugs includes a solid having a calcium salt of a bisphosphonate drug and a calcium salt of pentavalent phosphorus oxoacid. The composition is for sustained release of a bisphosphonate drug and the aqueous suspension of the solid is adapted to release the bisphosphonate drug into the patient over an extended period of time, for example over about two months or longer. The composition has a low solubility of less than about 0.05% in saline, by weight and as the bisphosphonic acid. The composition contains the calcium salt of the bisphosphonate drug in an amount of about 50% or less by weight. The particle size of the suspension composition ranges from about 1 to about 100 micrometers. The pH of the sterile pharmaceutical aqueous suspension composition ranges from about 6.0 to about 9.5. The weight ratio of calcium and phosphorus in the aqueous suspension ranges from about 0.5 to about 3.0.

BRIEF DESCRIPTION OF THE DRAWINGS

The above and other features and advantages of the present invention will be better understood by reference to the following detailed description when considered in conjunction with the accompanying drawings in which.

DETAILED DESCRIPTION OF THE INVENTION

According to one embodiment of the present invention, a sterile pharmaceutical composition comprises an aqueous suspension of a bisphosphonate drug. The pharmaceutical composition is a long term sustained release composition comprising an aqueous suspension of a solid including a salt of a bisphosphonate drug and a salt of pentavalent phosphorus oxoacid. The aqueous suspension of the solid is adapted to release the bisphosphonate drug into the patient over an extended period of time, for example over about two months or longer. The composition is suitable for intramuscular administration and is useful for the prevention and treatment of osteoporosis and other bone related diseases.

Surprisingly, Applicants have discovered that compositions of the present invention, namely suspensions of complex salts of bisphosphonic acid, produce significantly lower solubility (approximately 100 to 1000 times lower) compared to prior art calcium salts. This allows the formulations of the present invention to exhibit much slower and more long term sustained release profiles as illustrated in the examples outlined below. For example, as noted above, the aqueous suspension of the solid is adapted to release the bisphosphonate drug into the patient over an extended period of time, such as over about two months or longer.

In one embodiment, the bisphosphonate drug may have a general structure, in its acid form (bisphosphonic acid) of $(HO)_2PO—R—OP(OH)_2$, where R can include any group for the bisphosphonate, nonlimiting examples of which include 1-hydroxy-3-amino-1-propylidene (Pamidronic acid), 1-hydroxy-4-amino-butylidene (Alendronic acid), 1-hydroxy-3-(methylpentylamino)propylidene (Ibandronic acid), 1-hydroxy-2-(3-pyridinyl)-ethylene (Risedronic acid), 1-hydroxy-2-imidazol-1-yl-ethylene (Zoledronic acid), and (4-chloro-phenyl)-thio-methylene (Tiludronic acid).

According to one embodiment, the present invention is directed to a sustained release pharmaceutical composition comprising a solid including a salt of a bisphosphonate drug and a salt of pentavalent phosphorus oxoacid. The solid is suspended in an aqueous medium. The solid has solubility in saline of less than about 0.05% by weight as bisphosphonic acid. The solid has a particle size of less than about 100 micrometers, for example the solid may have a particle size ranging from about 10 to about 50 micrometers. The solid may be amorphous, crystalline (having a variety of crystal structures), or a mixture thereof. One nonlimiting example of a suitable aqueous medium is water for injection, U.S.P.

Nonlimiting examples of suitable salts for the composition include salts of calcium, zinc, magnesium and combinations thereof. The salt of the bisphosphonate drug may include, but is not limited to, normal salts, acidic salts, basic salts, anhydrous salts, hydrates and combinations thereof. The salt of pentavalent phosphorus oxoacid may include, but is not limited to, normal salts, acidic salts, basic salts, phosphates, pyrophosphates, metaphosphates, polyphosphates, anhydrous salts, hydrates and combinations thereof.

Nonlimiting examples of suitable salts of pentavalent phosphorus oxoacid include dicalcium phosphate dihydrate (DCPD), $CaHPO_4.2H_2O$; dicalcium phosphate anhydrate (DCPA), $CaHPO_4$; octacalcium phosphate (OCP), $Ca_8(HPO_4)_2(PO_4)_4.5H_2O$; α-tricalcium phosphate (α-TCP), $α-Ca_3(PO_4)_2$; β-Tricalcium phosphate (β-TCP), $β-Ca_3(PO_4)_2$; amorphous calcium phosphate (ACP), $Ca_x(PO_4)_y.nH_2O$; calcium-deficient hydroxyapatite (CDHA), $Ca_{10-x}(HPO_4)_x(PO_4)_{6-x}(OH)_{2-x}$ (x=0~1); hydroxyapatite (HA), $Ca_{10}(PO_4)_6(OH)_2$; and tetracalcium phosphate (TTCP), $Ca_4(PO_4)_2O$.

According to one embodiment, the composition has a weight ratio of calcium to phosphorus ranging from about 0.5 to about 3.0, for example, the weight ratio of calcium to phosphorus may range from about 1.5 to 2.5. The pH of the composition may range from about 6.0 to about 9.5, for example, the pH of the composition may range from about 6.5 to about 8.5. Optionally, the composition may also contain various inactive pharmaceutical excipients. Nonlimiting examples of suitable excipients include surfactants, suspending agents, dispersing agents, tonicity agents, preservatives, pH buffers, agents for adjusting osmotic pressure, agents for adjusting viscosity, agents for adjusting density, and mixtures thereof.

In one embodiment, the composition is a long term sustained release formulation of a solid comprising: (a) a salt of a bisphosphonate drug, and (b) a salt of pentavalent phosphorus oxoacid, wherein the solid is suspended in an aqueous solution to form a suspension. The salt of the bisphosphonate drug is present in the composition in an amount less than about 50% by weight, for example, the salt of the bisphosphonate drug is present in an amount ranging from about 5 to about 30%. One exemplary salt for the composition is a calcium salt. The weight ratio of calcium to phosphorus in the composition ranges from about 0.5 to about 3.0, for example, the weight ratio of calcium to phosphorus may range from about 1.5 to about 2.5. The solid has a particle size of less than about 100 micrometers, for example, the solid may have a particle size ranging from about 10 to about 50 micrometers. The aqueous solution may be water for injection, U.S.P. The aqueous suspension may have a pH ranging from about 6.0 to about 9.5, for example, the pH may range from about 6.5 to about 8.5. The aqueous suspension may contain one or more inactive pharmaceutical excipients including, but not limited to, surfactants, suspending agents, dispersing agents, tonicity agents, preservatives, pH buffers, agents for adjusting osmotic pressure, agents for adjusting viscosity, agents for adjusting density, and the like.

Certain compositions of the present invention provide long term sustained release of bisphosphonate drugs. In addition, certain compositions avoid various adverse side effects associated with oral administration of bisphosphonate drugs. The delivered dose of the inventive compositions is much smaller than the oral dose, which has high bioavailability, thereby avoiding many of the adverse side effects associated with high oral doses. The inventive sustained release compositions also substantially eliminate peak doses (over dose) and valley doses (under dose). The inventive compositions are convenient for patients and reduce tissue irritation due to their extremely low solubility.

As noted above and illustrated in the below examples, certain embodiments of the compositions of the present invention have improved sustained release profiles compared with prior art compositions. In particular, according to one embodiment of the present invention, the composition releases an initial bolus of less than about 10%. The initial bolus is defined as the amount of the drug released in the first three days after administration. For example, one embodiment of the present invention releases an initial bolus of about 8% (which is much lower that the prior art at about 55%), as illustrated in the Examples below.

According to another embodiment of the present invention, the composition releases a maximum concentration, or peak amount (denoted Cmax), of less than about 10 mcg/day. For example, one embodiment of the present invention has a Cmax of about 8 mcg/day, which is much lower than the prior art at 74 mcg/day.

In yet another embodiment, the composition releases the peak amount (Cmax) over an extended period of time. The time it takes to release Cmax is denoted tmax, and according to one embodiment, tmax is greater than about 10 days. For example, one embodiment of the present invention has a tmax of about 13 days, which is much longer than the prior art at 1 day.

According to still another embodiment of the present invention, it takes the composition an extended period of time to release 50% and 90% of the drug. The time it takes the composition to release 50% of the drug is denoted $N_{50}$, and the time it takes the composition to release 90% of the drug is denoted $N_{90}$. According to one embodiment, the composition has a $N_{50}$ of greater than about 15 days, and a $N_{90}$ of greater than about 35 days. For example, in one embodiment, the composition has a $N_{50}$ of about 16.6 days, and a $N_{90}$ of about 38.5 days, which are also much longer than the prior art, at 2.8 and 9 days respectively.

The compositions of the present invention can be prepared in many ways. In one embodiment, for example, the composition is prepared by co-precipitation. In another embodiment, the composition is prepared by co-crystallization. In yet another embodiment, the composition is prepared by diffusion. In still another embodiment, the composition can be prepared by infiltration or adsorption. The sustained release compositions of the present invention and methods of preparing the compositions are further illustrated in the following examples, which are provided for illustrative purposes only, and are not intended to limit the scope of the present invention.

Comparative Example 1

Preparation of Alendronate Calcium (AC)

For purposes of comparison with certain embodiments of the present invention, an alendronate calcium (AC) composition was prepared according to this example that does not include a salt of pentavalent phosphorus oxoacid.

2.03 g (6.3 mM) of sodium alendronate trihydrate was dissolved in 60 mL water. 0.94 g of calcium chloride dihydrate was dissolved in 30 mL water. Both solutions were cooled to room temperature.

To the alendronate solution, sodium hydroxide and calcium chloride solutions were simultaneously added to keep the pH of the solution at 7.0 until all the calcium chloride solution had been added. The precipitate was collected by filtration and washed with water. The solid was dried in an oven at 120° C. over night to obtain 1.5 g of alendronate calcium, denoted as $Ca_kY$ (where Y is the Alendronate anion). The mean value of k for the generated alendronate calcium at neutral solution (the pH of human blood) was 1.5±0.1. Chemically, $Ca_{1.5}Y$ corresponds to $Ca_3Y_2$. The solubility of $Ca_{1.5}Y$ in saline, as alendronic acid, was measured as 247 mcg/mL or 0.0247%.

The saline solubility measurement was performed as follows (unless otherwise described, all solubility of the complex products in saline were measured using the following procedures): the saline was pH buffered at pH=7.4. 200 mg of the product was added to 20 mL of the buffered saline. This solution was stirred at room temperature to reach equilibrium. The supernatant was separated by centrifugation and filtration through a 0.1 μm filter. The alendronate was measured by high performance liquid chromatography (HPLC).

Example 1

Preparation of Complex (Sosoloid) of Alendronate Calcium-Phosphate Calcium (AC-PC)

Phosphate salt is a commonly used salt of pentavalent phosphorus oxoacid. This example demonstrates the preparation of a complex or sosoloid of Alendronate Calcium-Phosphate Calcium (AC-PC) by co-precipitation according to one embodiment of the present invention.

4.06 g (12.5 mM) of sodium alendronate trihydrate and the same molar amount of monobasic sodium phosphate (anhydrous) 1.5 g (12.5 mM) were dissolved in 160 mL water to obtain Solution A. 4.75 g of calcium chloride dihydrate was dissolved in 50 mL water to obtain Solution B. Both Solutions A and B were cooled to room temperature. Solution B was added to the alendronate-phosphate solution (Solution A), and the mixture was mixed well to obtain Solution C. The pH of this clear Solution C was around 3.

IN sodium hydroxide and Solution C were simultaneously added to 300 mL of water at 40° C. while stirring, to keep the pH of the solution at 6.75 at 40° C. until all the Solution C was added. The precipitate was collected by filtration and washed with water. The solid was dried in an oven at 120° C. for more than 16 hours. 5.61 g of a calcium complex salt of alendronate and phosphate with a molecular ratio of 1:1 was thus obtained. Due to the presence of calcium phosphate, a complex or sosoloid of alendronate calcium-phosphate calcium (AC-PC) was generated. The active pharmaceutical ingredient (API) in the AC-PC complex is alendronate salt.

The same procedure was performed, but with varying molar ratios of sodium alendronate and monobasic sodium phosphate, i.e. n=3, 5, 6, 8, 10, 12, 15 and 20, to prepare complexes of AC-PC. The AC-PC complexes with varying amounts of API are summarized in Table 1 below:

TABLE 1

Preparation of AC-PC Complex by Co-precipitation

| Molar Ratio of AC-PC* | Reaction Condition | | API % as Alendronic acid | solubility in saline** | | |
|---|---|---|---|---|---|---|
| | Temperature (° C.) | pH | | in unit of mcg/mL | in % by weight | times lower than $Ca_3Y_2$ |
| 1:1 | 40 | 6.75 | 54.3 | 2.41 | 0.00024% | 102 |
| 1:3 | 40 | 6.75 | 30.2 | 1.14 | 0.00011% | 217 |
| 1:5 | 25 | 7.0 | 21.6 | 0.71 | 0.000071% | 348 |
| 1:5 | 40 | 6.75 | 21.7 | 0.75 | 0.000075% | 329 |
| 1:5 | 60 | 6.4 | 22.0 | 0.83 | 0.000083% | 298 |
| 1:6 | 40 | 6.75 | 20.0 | 0.61 | 0.000061% | 405 |
| 1:8 | 40 | 6.75 | 15.4 | 0.51 | 0.000051% | 484 |
| 1:10 | 40 | 6.75 | 12.6 | 0.44 | 0.000044% | 558 |
| 1:10 | 65 | 8.0 | 12.7 | 0.54 | 0.000054% | 457 |
| 1:12 | 40 | 6.75 | 11.3 | 0.35 | 0.000035% | 714 |
| 1:15 | 40 | 6.75 | 9.1 | 0.31 | 0.000031% | 797 |
| 1:20 | 40 | 6.75 | 6.2 | 0.20 | 0.000020% | 1235 |

*As the ratio of reactants: alendronate sodium vs. monobasic sodium phosphate
**At room temperature and as alendronic acid.

Figure 1:
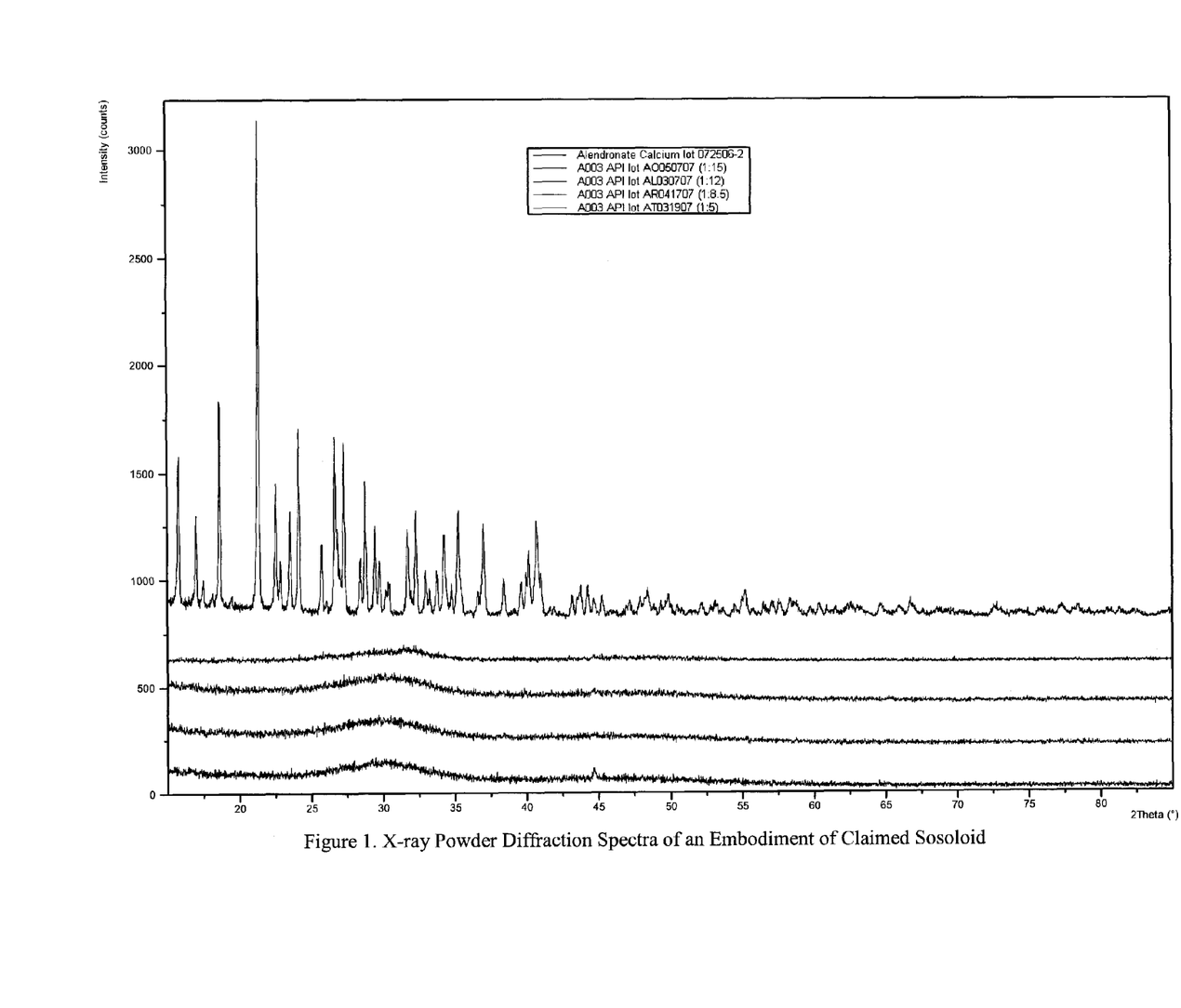
FIG. 1 is a graph of the solubility of an alendronate calcium-phosphate calcium complex according to one embodiment of the present invention based on the amount of active pharmaceutical ingredient in the complex.

The data in Table 1 shows that the solubility of the AC-PC complex, as alendronic acid, is surprisingly between 100 and 1200 times lower than that for alendronate calcium (AC) itself. For example, the solubility of the API in saline for an AC-PC complex with 12.6% API is only 0.44 mcg/mL or 0.000044%, which is 558 times lower than that for alendronate calcium, i.e. 247 mcg/mL, as reported in Comparative Example 1. This extremely low solubility of API for AC-PC complexes provides a base for a much better sustained release of the API. FIG. 1 demonstrates that the experimental solubility of AC-PC complexes is uniformly reduced while the amount of API in the AC-PC complex decreases.

The reactions of the above co-precipitation methods to prepare AC-PC complexes may be performed under different conditions, such as different pH values, temperatures, reactant mixing sequences, etc. However, the profile for obtaining complexes with low solubility of the API remains the same.

Example 2

Preparation of Complex of Risedronate Calcium and Phosphate Calcium (PC)

This example demonstrates that PC can also form complexes with calcium salts of another bisphosphonate drug, risedronate calcium.

0.61 g (2 mM) anhydrous sodium risedronate and 2.4 g monobasic sodium phosphate (anhydrous) were dissolved in 30 mL water. 5.6 g calcium chloride dihydrate were dissolved in 10 mL water. The risedronate-phosphate solution and calcium chloride solution were mixed at room temperature.

The risedronate-calcium-phosphate solution and 0.5N sodium hydroxide were simultaneously added to 100 mL water to maintain the pH at 7.00 until all the risedronate had been added. The precipitate was collected by filtration and washed with water. The solid was dried in an oven at 105° C. 3.93 g of calcium complex salt of Risedronate with phosphate were thus obtained.

Analysis indicates that the complex has an amount of the API (as risedronic acid) of 12.33%. The solubility of the API (as risedronic acid) at room temperature in saline of this complex was 2.8 mcg/mL or 0.00028%. This is a very low solubility and is suitable for sustained release of the bisphosphonate drug.

Example 3

Preparation of Complex of Zoledronate Calcium and Phosphate Calcium (PC)

This example demonstrates that PC can also form complexes with calcium salts of another bisphosphonate drug, zoledronate calcium.

0.27 g (1 mM) zoledronic acid and 0.6 gm (5 mM) monobasic sodium phosphate (anhydrous) were dissolved in 10 mL water. 1.5 g calcium chloride dihydrate was dissolved in 5 mL water. The zoledronate-phosphate solution and calcium chloride solution were mixed at room temperature. 0.05 g calcium chloride dihydrate and 0.3 g sodium chloride were added to 20 mL water. Sodium hydroxide and zoledronate-calcium-phosphate solution were simultaneously added to keep the pH at 7.00 at room temperature until all the zoledronate-phosphate solution was added. The precipitate was collected by filtration and washed with water. The solid was dried in an oven at 120° C. 1.15 g of calcium complex salt of zoledronate with phosphate was thus obtained in a molecular ratio of 1:5.

Analysis indicates that this complex had an amount of API (as zoledronic acid) of 24.1%. The solubility at room temperature in water of this complex, as zoledronic acid, was 7.5 mcg/mL or 0.00075%. This is a very low solubility as well.

Example 4

Preparation of Complex of AC and Pyrophosphate Calcium (PPC)

Pyrophosphate salt is also a common salt of pentavalent phosphorus oxoacid. This example demonstrates one exemplary method of preparing a complex of Alendronate Calcium-Pyrophosphate Calcium (AC-PPC) by co-precipitation.

0.81 g sodium alendronate trihydrate and 1.12 g sodium pyrophosphate decahydrate ($Na_4P_2O_7.10$ $H_2O$) were dissolved in 75 mL water. 1.21 g calcium chloride dihydrate was dissolved in 75 mL water. The temperature of the alendronate-pyrophosphate solution was brought to 40 to 50° C. Calcium chloride and sodium hydroxide solutions were simultaneously added to the alendronate-pyrophosphate solution while stirring to keep the pH at 7.4 until all the calcium chloride solution was added. The mixture was cooled to room temperature. The precipitate was collected by filtration and washed with water. The solid was dried in an oven at 105° C. overnight. 1.06 g of calcium complex salt of alendronate with pyrophosphate was thus obtained with a molecular ratio of 1:1.

Due to the presence of calcium pyrophosphate, a complex or sosoloid of alendronate calcium and pyrophosphate calcium (AC-PPC) was generated. The same procedure as above was performed, but with varying molar ratios of sodium alendronate and sodium pyrophosphate, i.e. n=2, 3, 5, and 10, to prepare more AC-PPC complexes. The AC-PPC complexes with varying amounts of the API are summarized in Table 2 below:

TABLE 2

Preparation of AC-PPC Complex by Co-precipitation

| Molar Ratio of AC-PPC* | Reaction Condition | | API % as Alendronic acid | solubility in saline** | |
|---|---|---|---|---|---|
| | Temperature (° C.) | pH | | in unit of mcg/mL | in % by weight |
| 1 | 50 | 7.4 | 36.7 | 18.2 | 0.00182% |
| 2 | 40 | 7.4 | 28.4 | 5.3 | 0.00053% |
| 3 | 50 | 7.4 | 19.8 | 3.9 | 0.00039% |
| 5 | 50 | 7.4 | 14.4 | 0.8 | 0.00008% |
| 10 | 50 | 7.4 | 7.9 | 0.4 | 0.00004% |

*As the ratio of reactants: alendronate sodium vs. sodium pyrophosphate
**At room temperature and as alendronic acid.

The AC-PPC complex shows the same characterization for solubility of the API in saline as that for the AC-PC complex. Specifically, the AC-PPC complexes have very low solubility for the API, ranging from 0.00001% to 0.001%. Also, the lower amount of the API in the complexes, the lower the solubility of the API.

Example 5

Preparation of Complex of AC and Tripolyphosphonate Calcium (TPC)

This example demonstrates that calcium salts of another pentavalent phosphorus oxoacid, tripolyphosphonate, can also form a Alendronate Calcium-Tripolyphosphonate Calcium (AC-TPC) complex by co-precipitation.

2.03 g sodium alendronate trihydrate (6.25 mmol) and 6.9 g sodium tripolyphosphate, $Na_5P_3O_{10}$ were added to 100 mL water, and the mixture was stirred until all dissolved. 10.34 g calcium chloride dihydrate were dissolved in 200 mL water. The calcium chloride solution was heated to 40° C. and the pH was adjusted to 7.0. The alendronate-tripolyphosphonate solution was added into the calcium chloride solution dropwise, keeping the pH of the resulting solution at 7.0 by adding 1N NaOH. The precipitate was collected by filtration and washed with water. The solid was dried in an oven at 120° C. overnight. 8.82 g of calcium complex salt of alendronate with tripolyphosphate was thus obtained.

Analysis indicates that this complex has 12.6% API, as alendronic acid. The solubility of the API (as alendronic acid) in saline at room temperature for this complex was 2.69 mcg/mL or 0.000269%. Therefore, AC-TPC is also a complex with very low solubility of the API.

Example 6

Preparation of Complex of Alendronate Zinc-Phosphate Zinc

The metal in the AC-PC complex can be replaced by other divalent metals such as zinc, magnesium, etc. This example demonstrates preparation of complexes of alendronate zinc-phosphate zinc by co-precipitation.

3.25 g of sodium alendronate trihydrate and 1.42 g of dibasic sodium phosphate (anhydrous) were dissolved in 100 mL water. The solution temperature was kept at 50° C. on a hot plate. This temperature was maintained throughout the process. While stirring, a solution of 5.8 g of zinc acetate dihydrate in 50 mL of water was added to the alendronate-phosphate solution. The pH of the solution was kept at 7.4 by adding sodium hydroxide solution simultaneously until all the zinc acetate solution was added. The precipitate was collected by filtration and washed with water. The solid was then dried at 120° C. overnight. 5.28 g of zinc complex salt of alendronate and phosphate with a molecular ratio of 1:1 was thus obtained. The solubility of the API (as alendronic acid) in saline at room temperature for this complex is 2.4 mcg/mL, i.e. 0.00024%. It also has a very low solubility of the API.

Example 7

Preparation of AC-PC Complex by Adsorption

Besides the co-precipitation method, the AC-PC complexes can be prepared by various other methods, such as, for example, adsorption and diffusion. In this example, a commercial hydroxyapatite (HA), which is one of various forms of phosphate calcium, is used to prepare an AC-PC complex by adsorption.

0.66 g (2.0 mM) sodium alendronate trihydrate was added to 50 mL water, and the solution was stirred until all dissolved. The pH was adjusted to the range of 8.0 to 8.5. 2 g of hydroxyapatite (Spectrum, CA165) was added and the solution was stirred at room temperature for 20 hr. After stirring, 200 mL of water was added and the solid was separated by filtration. The solid was transferred, 200 mL of water was added, and the solid was filtered again. This process was repeated one more time. The solid product was dried at 105° C. for more than 3 hrs. The complex had 8.8% API, as alendronate acid, and its solubility of the API at room temperature in saline was 7.9 mcg/mL, or 0.00079%.

Experimental Example 1

Pharmacokinetic (PK) study of AC-PC Complex on Rat Model

In this study, the AC-PC complex with 12.6% API prepared in Example 1 was intramuscularly injected into Group A female Sprague-Dawley rats ($n_A$=12). The age of the female rats was about 4 months. Each rat was injected with 8 mg of the AC-PC complex, which contains 1 mg of API (as alendronic acid). The PK profile for long-term sustained release was studied through urine excretion of alendronate. Urine samples were collected over 24 hour intervals. The alendronate from the AC-PC complex excreted in the urine was first precipitated by calcium phosphate co-precipitation, then derivatized by 2,3-naphthalenedialdehyde, and determined by reverse phase high performance liquid chromatography (HPLC) equipped with a fluorescence detector.

A prior art active control, alendronate calcium, prepared in Comparative Example 1, was used in this PK study in Group B female rats ($n_B$=10). The active control had a solubility of API in saline of 404 mcg/mL or 0.0404%, which is much higher than that for the AC-PC complexes of Example 1. Table 3 summarizes the daily urine excretion of alendronate, as alendronic acid, after the administration of the AC-PC complex of Example 1 and the active control.

Figure 2:
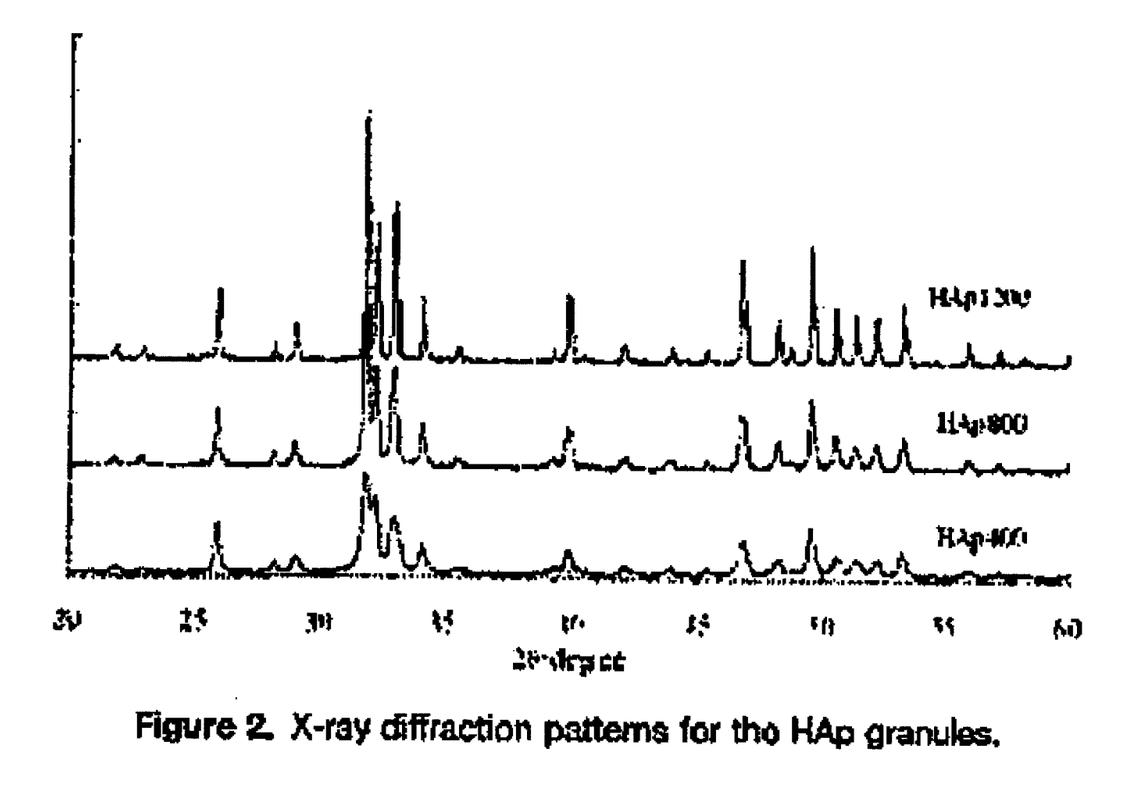
FIG. 2 is a graph comparing rat daily urine excretions over time of an alendronate calcium-phosphate calcium complex according to one embodiment of the present invention and an active prior art control.

FIG. 2 gives the curve of rat urine daily excretion versus the number of days after administration for both the AC-PC complex of Example 1 (blue curve) and the active control of the prior art (red curve). The figure demonstrates that the complexes according to certain embodiments of this invention can provide significantly better and longer sustained release effects than the prior art.

TABLE 3

Daily Rat Urine Excretion of Alendronate

| Days after administration | Prior Art mcg/day | This Invention mcg/day |
|---|---|---|
| 0 | 0.1 | 0.0 |
| 1 | 73.5 | 6.7 |
| 3 | 17.5 | 5.1 |
| 5 | 16.7 | 4.7 |
| 7 | 7.5 | 6.5 |
| 10 | 5.5 | 7.4 |
| 13 | | 8.3 |
| 16 | 1.4 | |
| 17 | | 7.1 |
| 21 | | 5.8 |
| 23 | 0.5 | |
| 25 | | 4.2 |
| 30 | | 2.8 |
| 35 | | 1.8 |
| 42 | | 1.3 |
| 49 | | 0.8 |
| 56 | | 0.5 |
| 63 | | 0.3 |
| 70 | | 0.2 |

As summarized by Table 4 below, the two products, AC-PC complexes of this invention and the prior art (AC only) were studied with the same animal model (rat), at the same dose (1 mg per rat) and demonstrated the same amount of total excretion. The tested compositions of this invention (AC-PC complexes) showed much better sustained release effects, as discussed below:

(1) Initial Bolus: 7 Times Lower

Initial bolus is defined as the percentage of the amount released in the first 3 days based on the total released amount. For a sustained release, small initial bolus is desired to reduce overdose and to avoid the surge of possible adverse effects caused by a high initial bolus. Certain embodiments of this invention release only 8% of total released drug in the first 3 days (measured by rat urine excretion). However, the prior art product releases 55% of total released drug during the same period, i.e. more than half of the drug is released in the first 3 days. Therefore, the initial bolus for certain embodiments of this invention is seven (7) times lower than that for the prior art.

(2) Cmax: 9 Times Lower

Sustained release avoids high peak amounts of the drugs in the human body. The peak amount is denoted Cmax. A good sustained release drug should have lower Cmax to reduce possible toxicity and adverse effects caused by a high Cmax. This example used urine excretion as the indication of sustained release. Cmax corresponds to the maximum daily urine excretion, which measured 74 mcg/day for the prior art and 8 mcg/day for the tested complexes of this invention. Namely, certain embodiments of this invention have a Cmax nine (9) times lower than the product of the prior art.

(3) tmax: 13 Times Delayed

The time when Cmax appears is defined as tmax. Long-term sustained release drugs might also have a delayed tmax. The tmax was 1 day for the prior art and 13 days for the tested complexes of this invention. Namely, certain embodiments of the present invention have a tmax thirteen (13) times more delayed than the product of the prior art.

TABLE 4

A Comparison of Sustained Release Parameters

| Items | Prior Art | This Invention | Advantage of This Invention |
|---|---|---|---|
| Model | Rats | Rats | |
| Administration | IM | IM | |
| # of Rats | 10 | 12 | |
| Dose, mg | 1000 | 1000 | the same |
| Total Excretion | 230 | 210 | the same |
| Total Net Bone Absorbed | 770 | 790 | the same |
| Net Bone Absorption Rate, % | 77% | 79% | the same |
| Initial Bolus (in the first 3 days), % of Released Drug | 55% | 8% | 7 times lower |
| $C_{max}$ for Released Drug (Daily Excretion) | 74 | 8 | 9 times lower |
| tmax for Released Drug | 1 | 13 | 13 times longer |
| Number of days to release 50% of API | 2.8 | 16.6 | 6 times longer duration |
| Number of days to release 90% of API | 9.0 | 38.5 | 4 times longer duration |

(4) Number of Days to Release 50% of the Drug: 6 Times Longer

The effect of a sustained release drug can be characterized by the number of days it takes to release 50% of the drug, which may be denoted as $N_{50}$. Long-term sustained release drugs should have a longer $N_{50}$. The $N_{50}$ was 2.8 days for the prior art and 16.6 days for the tested compositions of this invention. Thus, certain embodiments of this invention have a $N_{50}$ six (6) times longer than the product of the prior art.

(5) Number of Days to Release 90% of the Drug: 4 Times Longer

The effect of a sustained release of a drug can also be characterized by the number of days it takes to release 90% of the drug, which may be denoted as $N_{90}$. A long-term sustained release drug should have a longer $N_{90}$. The $N_{90}$ was 9.0 days for the prior art product and 38.5 days for the tested compositions of this invention. Thus, certain embodiments of this invention have a $N_{90}$ four (4) times longer than the product of the prior art.

Experimental Example 2

Efficacy Study of AC-PC Complex on Rat Model

This Experimental Example demonstrates the efficacy of long-term sustained release of certain AC-PC complexes of this invention. In this study, the AC-PC complex formulations were intramuscularly injected into female Sprague-Dawley rats. Rats used in this study underwent overiectomy operations (OVX). The age of the female rats was around 2½ months when the surgical operation was performed. A 2½-month recovery period was allowed after overiectomy/sham operations to ensure post-surgical recovery and to establish hypoestrogenemia and osteoporosis before treatment with the AC-PC complexes.

The rats were divided into three (3) groups:
Group-A: treated by AC-PC complexes at lower doses, 0.25 mg (alendronic acid)

Group-B: treated by AC-PC complexes at higher doses, 1.0 mg (alendronic acid)

Group-C: treated by placebos (saline)

The treatment drugs or placebos (saline) were injected once every 2 months. Three injections were administrated at 0, 60 and 120 days.

Figure 3:
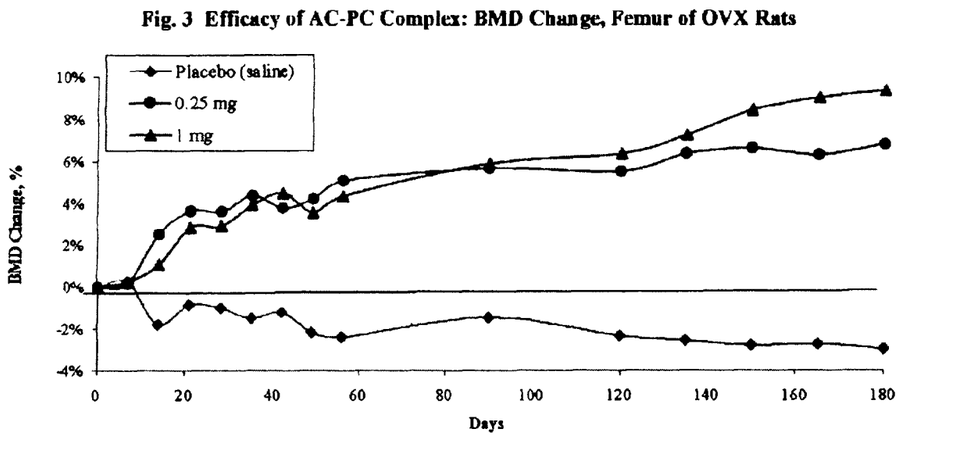
FIG. 3 is a graph of changes in rat bone mineral density over time after administration of two different dosages of an alendronate calcium-phosphate calcium complex according to one embodiment of the present invention and a saline placebo.

The AC-PC complexes used in this Example had 12.6% of the API and were prepared as in Example 1. The bone-preserving effects of the complex were measured as percent change in bone mineral density (BMD) by Dual X-Ray Absorptiometry (DEXA) in the right femur 4.3 mm from the proximal end in an area of 8.6×7.2 mm. The BMD for all rats was measured at day 0, 7, 14, 28, 35, 42, 49, 56, 90, 120, 135, 150, 165 and 180. The obtained data is summarized in Table 5 and FIG. 3.

TABLE 5

Mean BMD Change, Right Femur of OVX Rats

| | | Rat Group | | | | |
|---|---|---|---|---|---|---|
| | | A | B | | C | |
| | | Type of Rats | | | | |
| | | OVX | OVX Treatment | | OVX | |
| | | Saline | AC-PC complex | | AC-PC complex | |
| | | Dose, mg, as alendronic acid | | | | |
| | | Placebo | 0.25 × 3 | | 1 × 3 | |
| Items | | Mean S.D. | Mean | S.D. | Mean | S.D. |
| Measured | 0 | 0.0%  0.0% | 0.0% | 0.0% | 0.0% | 0.0% |
| at Days | 7 | 0.3%  1.4% | 0.2% | 1.7% | 0.3% | 1.0% |
| after | 14 | −1.8%  2.3% | 2.5% | 2.3% | 1.1% | 1.6% |
| administration | 21 | −0.9%  2.2% | 3.6% | 2.3% | 2.9% | 1.2% |
| | 28 | −1.0%  2.8% | 3.6% | 2.5% | 2.9% | 1.9% |
| | 35 | −1.5%  2.6% | 4.4% | 2.6% | 3.9% | 1.9% |
| | 42 | −1.2%  3.1% | 3.8% | 3.1% | 4.5% | 2.3% |
| | 49 | −2.2%  2.8% | 4.2% | 3.2% | 3.6% | 1.8% |
| | 56 | −2.4%  3.0% | 5.1% | 2.6% | 4.4% | 1.7% |
| | 90 | −1.5%  3.8% | 5.7% | 2.1% | 5.9% | 1.8% |
| | 120 | −2.3%  3.7% | 5.5% | 3.2% | 6.4% | 2.3% |
| | 135 | −2.5%  2.9% | 6.4% | 3.1% | 7.3% | 2.3% |
| | 150 | −2.8%  2.6% | 6.6% | 4.2% | 8.4% | 2.4% |
| | 165 | −2.7%  3.1% | 6.3% | 3.2% | 9.0% | 2.2% |
| | 180 | −3.0%  2.8% | 6.8% | 3.6% | 9.4% | 2.5% |

The $AUC_{0,0180}$ (area under curve) for all 3 rat groups are summarized in Table 6 below. The p-value for efficacy is evaluated with placebo group (Group C). All p-values are significantly less than 0.05, which confirmed the efficacy of the tested complex for osteoporosis through long-term sustained release.

TABLE 6

Efficacy of Long-term Sustained Release Complex

| Treatment | Dose mg/Rat | Type of Rats | Rat Group | # of Rats n | $AUC_{0,180}$*, %-day Mean S.D | p-value vs. A |
|---|---|---|---|---|---|---|
| Placebo: Saline | — | OVX | A | 12 | −3.5  4.8 | — |
| AC-CDHA | 0.25 × 3 | OVX | B | 12 | 9.1  4.5 | <0.0001 |

TABLE 6-continued

Efficacy of Long-term Sustained Release Complex

| Treatment | Dose mg/Rat | Type of Rats | Rat Group | # of Rats n | $AUC_{0,180}$*, %-day Mean S.D | p-value vs. A |
|---|---|---|---|---|---|---|
| AC-CDHA | 1 × 3 | OVX | C | 12 | 10.0  2.9 | <0.0001 |

*Negative AUC indicates decrease in BMD over time.

Experimental Example 3

Evaluation of Tissue Tolerance (TT) of AC-PC Complex by Rat Model

The objective of this Example is to evaluate the local tissue tolerance, and both macroscopic and microscopic (histopathological) examination of tissue toxicity/reaction of AC-PC complexes were performed.

Bisphosphonate salt can cause tissue damage and irritation following intramuscular injection. However, the solubility of bisphosphonate for AC-PC complexes according to certain embodiments of this invention is reduced by 100 to 1000 times compared to alendronate calcium according to the prior art. Therefore, the tissue tolerance level for AC-PC complexes may reach the same level that is acceptable for the FDA and patients.

(1) Study Procedure

The AC-PC complexes, with 12.6% API, prepared as in Example 1, was used for tissue tolerance evaluation by a rat model. 0.9% saline was used as a negative control. A medroxyprogesterone acetate (MPA) suspension injection (150 mg/mL) (which is an FDA approved sustained release drug) was used as a reference control.

A total of 70 rats were used in this study. Thirty five (35) rats, assigned in Group T, were intramuscularly (IM) injected with 0.25 mL of the AC-PC complex in the right thigh and with 0.25 mL of 0.9% saline in the left thigh. Another 35 rats, assigned in Group R, were IM injected with 0.25 mL MPA (the reference control) in the right thigh. Rats were examined for general health conditions prior to injection on Day 0. All tissue response evaluations were performed at 1, 7, 14, 28, 56, 84, and 120 days post injection. Five (5) rats from each group (T and R) were sacrificed at each post injection time point listed above.

(2) Macroscopic Edema and Erythema Examination

Macroscopic examinations of the treatment sites for evidence of any tissue reaction such as erythema and edema were performed. The edema and erythema scoring system was adapted from USP<88> Biological Reactivity Tests, in vivo.

To evaluate macroscopic edema and erythema, Mean Tissue Reaction Score (MTRS) was used. The MTRS is the average of all edema and erythema scores. MTRS for all three (3) treatments at 7 evaluation points are listed in Table 7 below.

As shown in Table 7, throughout the study period, the macroscopic edema and erythema evaluations identified little to no tissue irritation observed for the AC-PC complex and the reference control MPA as well as the negative control. The macroscopic MTRS score for the AC-PC complex was zero (0) indicating it is a non-irritant drug through out the 120-day study period with respect to edema and erythema.

TABLE 7

Summary of Mean Tissue Reaction Scores (MTRS)

| Post Injection Day | # of Rats in groups T & R | AC-PC Complex | | Saline, Negative Control | | MPA, Reference Control | |
|---|---|---|---|---|---|---|---|
| | | Edema | Erythema | Edema | Erythema | Edema | Erythema |
| Day 1 | 35 | 0 | 0 | 0 | 0 | 0 | 0 |
| Day 7 | 30 | 0 | 0 | 0 | 0 | 0 | 0 |
| Day 14 | 25 | 0 | 0 | 0 | 0 | 0 | 0 |
| Day 28 | 20 | 0 | 0 | 0 | 0 | 0 | 0 |
| Day 56 | 15 | 0 | 0 | 0 | 0 | 0 | 0 |
| Day 84 | 10 | 0 | 0 | 0 | 0 | 0 | 0 |
| Day 120 | 5 | 0 | 0 | 0 | 0 | 0 | 0 |
| Macroscopic MTRS | | 0 | | 0 | | 0 | |

Score:
0—None,
1—Slight,
2—Well-defined,
3—Moderate,
4—Severe (3) Microscopic Histopathological Examination Microscopic evaluation was performed using a 0 through 4 grading system that fulfills the biologically relevant aspects of ASTM F 981 (2004) and ISO 10993-6:1994(E) guidelines.

The mean histopathological examination score (MHES) was calculated using an average of all five (5) tissue histopathological examination scores at the same post injection date. The MHESs for all three (3) treatments at 7 evaluation points are listed in Table 8 below.

TABLE 8

Summary of Mean Histopathological Examination Score* (MHES)

| Post Injection Day | AC-PC Complex (T) | Saline Negative Control | MPA (R) | Difference Between T and R, T − R |
|---|---|---|---|---|
| 1 | 8.8 | 2.8 | 10.5 | −1.7 |
| 7 | 7.4 | 1.6 | 8.8 | −1.4 |
| 14 | 12.0 | 0.6 | 9.6 | 2.4 |
| 28 | 16.2 | 0.6 | 13.6 | 2.6 |
| 56 | 12.2 | 0 | 7.4 | 4.8 |
| 84 | 7.6 | 0 | 8.5 | −0.9 |
| 120 | 5.6 | 0 | 8.8 | −2.1 |

*Scale for Conclusion: Nonirritant (0.0-2.9), Slight Irritant (3.0-8.9), Moderate Irritant (9.0-15.0), Severe Irritant (≥15.1)

As shown in Table 8, the microscopic histopathological examination scores for the AC-PC complex were very similar to those for the Reference Control and MPA over time. Since the MHESs decreased over time, resorption of the AC-PC complex with corresponding diminution of the inflammatory reaction with time was likely.

(4) Conclusion for Tissue Tolerance

In summary, based on both macroscopic and microscopic evaluation, the AC-PC complexes according to certain embodiments of the present invention may be associated with an acceptable level of tissue tolerance as compared to the commercially and clinically available Reference Control (MPA).

The examples and experiments described above are presented solely for illustrative purposes and are not meant to limit the scope of the invention in any way. While the invention has been described with reference to certain exemplary embodiments, it is understood that the invention is not limited to the described embodiments since those of ordinary skill in the art would recognize that many changes and modifications may be made to the described embodiments without departing from the spirit and scope of the invention, as defined in the appended claims.

What is claimed is:

1. A pharmaceutical composition suitable for injection as an aqueous suspension for sustained release of a bisphosphonate drug, the composition comprising:
   an amorphous sosoloid containing a salt of a bisphosphonate drug comprising alendronate calcium and a salt of a pentavalent phosphorus oxoacid comprising phosphate calcium, the amorphous sosoloid having a solubility in saline of less than 0.05% by weight as bisphosphonic acid.

2. The pharmaceutical composition according to claim 1, wherein the salt of the bisphosphonate drug is present in an amount of less than about 50% by weight based on the total weight of the amorphous sosoloid.

3. The pharmaceutical composition according to claim 1, wherein a weight ratio of calcium to phosphorus ranges from about 0.5 to about 3.0.

4. The pharmaceutical composition according to claim 1, wherein the amorphous sosoloid has an average particle size of less than about 100 micrometers.

5. The pharmaceutical composition according to claim 1, wherein the amorphous sosoloid is suspended in an aqueous medium to form an aqueous suspension.

6. The pharmaceutical composition according to claim 1, wherein the aqueous suspension has a pH ranging from about 6.0 to about 9.5.

7. The pharmaceutical composition according to claim 1, wherein said aqueous suspension further comprising at least one inactive pharmaceutical excipient.

8. The pharmaceutical composition according to claim 7, wherein the inactive pharmaceutical excipient is selected from the group consisting of surfactants, suspending agents, dispersing agents, tonicity agents, preservatives, pH buffers, agents for adjusting osmotic pressure, agents for adjusting viscosity and agents for adjusting density.

9. A pharmaceutical composition suitable for injection as an aqueous suspension for sustained release of a bisphosphonate drug, the composition comprising:
   An amorphous sosoloid containing a calcium salt of a bisphosphonate drug comprising alendronate and a calcium salt of pentavalent phosphorus oxoacid comprising phosphate, wherein:

(a) the calcium salt of the bisphosphonate drug is present in an amount of less than about 50% by weight based on the total weight of the amorphous sosoloid,
(b) the amorphous sosoloid has a solubility in saline of less than about 0.00182% by weight as bisphosphonic acid,
(c) the amorphous sosoloid has a particle size ranging from about 1 to about 100 micrometers,
(d) the weight ratio of calcium to phosphorous has a value of from about 0.5 to about 3.0, and
(e) when suspended in an aqueous medium, the amorphous sosoloid forms an aqueous suspension having a pH of from about 6.0 to about 9.5.

* * * * *